(12) United States Patent
Kirsch et al.

(10) Patent No.: US 8,307,978 B2
(45) Date of Patent: Nov. 13, 2012

(54) KNOTLESS ENDOSTITCH PACKAGE

(75) Inventors: David Kirsch, Madison, CT (US); Matthew J. Chowaniec, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/036,053

(22) Filed: Feb. 28, 2011

(65) Prior Publication Data

US 2011/0215006 A1   Sep. 8, 2011

Related U.S. Application Data

(60) Provisional application No. 61/309,568, filed on Mar. 2, 2010.

(51) Int. Cl.
*A61B 17/06* (2006.01)
*B65D 85/24* (2006.01)
*B65D 73/00* (2006.01)
*B65D 6/04* (2006.01)

(52) U.S. Cl. ....... 206/63.3; 206/339; 206/409; 206/486; 206/564

(58) Field of Classification Search ................. 206/63.3, 206/380, 350, 574, 564, 339, 486, 409; 81/53.2, 81/52
See application file for complete search history.

(56) References Cited

U.S. PATENT DOCUMENTS

| | | | |
|---|---|---|---|
| 2,615,565 A | 10/1952 | Bower et al. | |
| 3,495,703 A | 2/1970 | Calabrese | |
| 3,972,418 A | 8/1976 | Schuler et al. | |
| 4,424,898 A | 1/1984 | Thyen et al. | |
| 4,572,363 A | 2/1986 | Alpern | |
| 4,961,498 A * | 10/1990 | Kalinski et al. | 206/339 |
| 4,967,902 A | 11/1990 | Sobel et al. | |
| 5,052,551 A | 10/1991 | Cerwin et al. | |
| 5,056,658 A | 10/1991 | Sobel et al. | |
| 5,099,994 A | 3/1992 | Kalinski et al. | |
| 5,154,283 A | 10/1992 | Brown | |
| 5,165,217 A | 11/1992 | Sobel et al. | |
| 5,213,210 A | 5/1993 | Cascio et al. | |
| 5,228,565 A | 7/1993 | Sinn | |
| 5,230,424 A | 7/1993 | Alpern et al. | |
| 5,236,083 A | 8/1993 | Sobel et al. | |
| 5,249,671 A | 10/1993 | Sinn | |
| 5,249,673 A | 10/1993 | Sinn | |
| 5,271,495 A | 12/1993 | Alpern | |
| 5,284,240 A | 2/1994 | Alpern et al. | |
| 5,301,801 A | 4/1994 | Sinn | |
| 5,350,060 A | 9/1994 | Alpern et al. | |
| 5,392,903 A | 2/1995 | Sinn | |

(Continued)

FOREIGN PATENT DOCUMENTS

EP   0726062 A2   8/1996

OTHER PUBLICATIONS

European Search Report for EP 11250230.7-1269 date of completion is Jun. 28, 2011 (3 pages).

*Primary Examiner* — J. Gregory Pickett
*Assistant Examiner* — James M Van Buskirk

(57) ABSTRACT

A suture loading package including a body portion including a securement structure for one or more lengths of suture such that the one or more lengths of suture can be stored prior to use. The suture loading package is configured and adapted to facilitate transferring each of the lengths of suture to a suture loading mechanism.

13 Claims, 6 Drawing Sheets

U.S. PATENT DOCUMENTS

| | | |
|---|---|---|
| 5,462,162 A | 10/1995 | Kaplan et al. |
| 5,472,081 A | 12/1995 | Kilgrow et al. |
| 5,478,344 A | 12/1995 | Stone et al. |
| 5,478,345 A | 12/1995 | Stone et al. |
| 5,503,266 A | 4/1996 | Kalbfeld et al. |
| 5,533,611 A | 7/1996 | Bordighon et al. |
| D374,284 S | 10/1996 | Stone et al. |
| D374,285 S | 10/1996 | DeFonzo et al. |
| 5,575,382 A | 11/1996 | Sobel et al. |
| D378,131 S | 2/1997 | Stone et al. |
| 5,615,766 A | 4/1997 | Gemma et al. |
| 5,628,395 A | 5/1997 | Daniele et al. |
| 5,655,652 A | 8/1997 | Sobel et al. |
| 5,667,155 A | 9/1997 | Cerwin et al. |
| 5,669,490 A | 9/1997 | Colligan et al. |
| 5,728,107 A | 3/1998 | Zlock et al. |
| 5,733,293 A | 3/1998 | Scirica et al. |
| 5,755,729 A | 5/1998 | de la Torre et al. |
| 5,769,214 A | 6/1998 | Zatarga |
| 5,819,918 A | 10/1998 | Scanlon |
| 5,833,055 A | 11/1998 | Cerwin et al. |
| 5,887,706 A | 3/1999 | Pohle et al. |
| 5,906,273 A | 5/1999 | Pohle et al. |
| 6,047,815 A | 4/2000 | Cerwin et al. |
| 6,076,659 A | 6/2000 | Baumgartner et al. |
| 6,098,796 A | 8/2000 | Januzeli et al. |
| 6,135,272 A | 10/2000 | Sobel et al. |
| 6,260,699 B1 | 7/2001 | Kaplan et al. |
| 6,464,071 B2 | 10/2002 | Baumgartner |
| 6,481,568 B1 | 11/2002 | Cerwin et al. |
| 6,533,112 B2 | 3/2003 | Warnecke |
| 6,644,469 B2 | 11/2003 | Alpern |
| 2004/0050721 A1 | 3/2004 | Roby et al. |
| 2005/0035007 A1 | 2/2005 | Kennedy et al. |
| 2006/0226031 A1 | 10/2006 | Kennedy et al. |
| 2007/0227914 A1 | 10/2007 | Cerwin et al. |
| 2007/0256945 A1 | 11/2007 | Kennedy et al. |
| 2008/0185752 A1 | 8/2008 | Cerwin et al. |
| 2009/0205987 A1 | 8/2009 | Kennedy et al. |
| 2009/0210006 A1 | 8/2009 | Cohen et al. |
| 2009/0250356 A1 | 10/2009 | Kirsch et al. |
| 2009/0312773 A1 | 12/2009 | Cabrera et al. |
| 2010/0084294 A1 | 4/2010 | Kirsch et al. |

* cited by examiner

KNOTLESS ENDOSTITCH PACKAGE

CROSS REFERENCE TO RELATED APPLICATIONS

This application claims priority to, and benefit of, U.S. Provisional Application Ser. No. 61/309,568, filed Mar. 2, 2010. The disclosure of this application is hereby incorporated by reference in its entirety.

BACKGROUND

1. Technical Field

The present disclosure relates to a package for storing one or more lengths of suture. In particular, the package is configured and adapted to store one or more lengths of suture and to transfer each of the lengths of suture to a suture loading mechanism.

2. Background of Related Art

Many surgical procedures involve the placement of sutures through tissue. To this end, various suture packages have been developed to hold suture needles and associated lengths of suture for use during a surgical procedure.

It is often advantageous to place a plurality of sutures in a tissue section. Accordingly, it is desirable that a suture package facilitate the repeated loading of needle-suture combinations onto a suturing apparatus.

SUMMARY

The present disclosure discloses a suture loading package including a body portion, a securement structure disposed within the body portion that is adapted and configured to releasably secure a length of suture within the body portion. An opening at a proximal end of the body portion is adapted and configured to receive the length of suture therethrough. A hub may be disposed at or near the proximal end of the body portion that is configured and adapted to receive a suture loading mechanism thereon. The securement structure may include one or more protrusions. The one or more protrusions may define a path about which the length of may be placed. Alternatively or additionally, each of the protrusions may releasably secure the length of suture thereon by facilitating placement of a looped portion of the length of suture about the protrusion. One or more posts may be configured and adapted to frictionally and releasably secure the length of suture therein. For example, the post may include a channel therethrough to receive the length of suture therein or therethrough.

These and other features of the present disclosure will be more fully described with reference to the appended figures.

BRIEF DESCRIPTION OF THE DRAWINGS

By way of description only, embodiments of the present disclosure will be described with reference to the accompanying drawings, in which.

DETAILED DESCRIPTION

Figure 1:
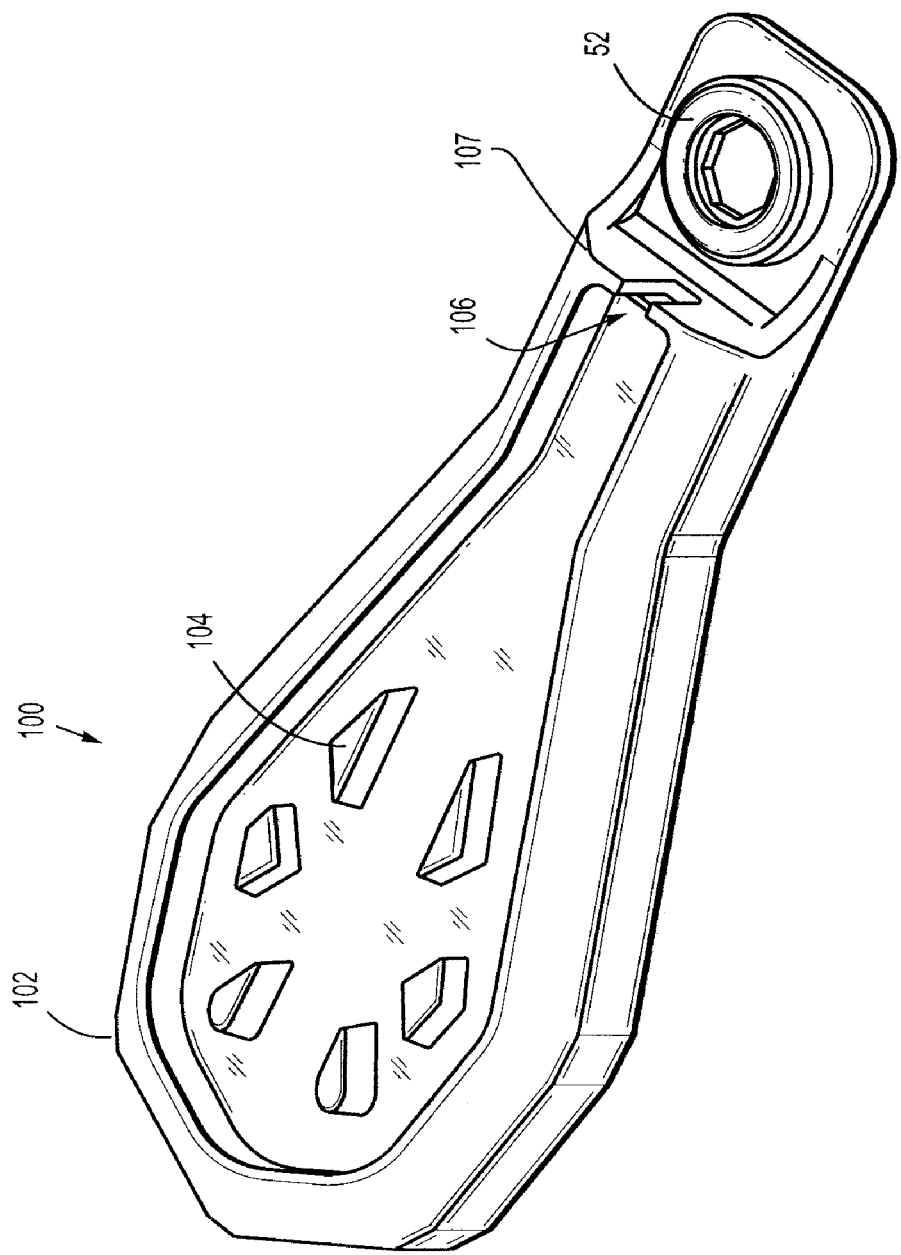
FIG. 1 is a perspective view of a suture loading package in accordance with the present disclosure.

Particular embodiments of the present disclosure will be described herein with reference to the accompanying drawings. In the figures and in the description that follows, in which like reference numerals identify similar or identical elements, the term "proximal" will refer to the end of the apparatus that is closest to the operator during use, while the term "distal" will refer to the end that is farthest from the operator during use.

Referring now to FIGS. 1-5, embodiments of a suture loading package that is configured and adapted to store one or more lengths of suture and to transfer each length of suture to a suture loading mechanism will now be described. In particular embodiments, a barbed suture may be employed. Suitable barbed sutures include those disclosed by U.S. patent application Ser. No. 12/361,962, which was filed on Jan. 29, 2009, the contents of which are hereby incorporated by reference in its entirety.

The suture loading package 100 will now be described with reference to FIG. 1. The suture loading package 100 generally includes a body portion 102. The body portion 102 may be ergonomically shaped to facilitate grasping of the suture loading package by a user. The shape of the body portion 102 may be, but is not limited to, a bulbous, round, or an arcuate shape such as that shown in FIG. 1. Advantages of a round shaped body portion 102 include less memory in the suture stored therein.

Disposed at or near a proximal end 107 of the body portion 102 is an opening 106 that is configured and adapted to receive a length of suture S (FIG. 2) therethrough. Each length of suture S may include an end effector, such as a looped portion 1 at a first end and be associated with a needle 12 at a second end. A hub 52 is located at or near the proximal end 107 and is configured and adapted to receive a suture needle loading mechanism 50 (FIG. 2) thereon. The suture needle loading mechanism 50 facilitates loading of the needle 12 positioned at the second end of the length of suture S onto a desired surgical apparatus by facilitating the reception of an end effector of the desired surgical apparatus such that the end effector may receive the needle 12.

Figure 6:
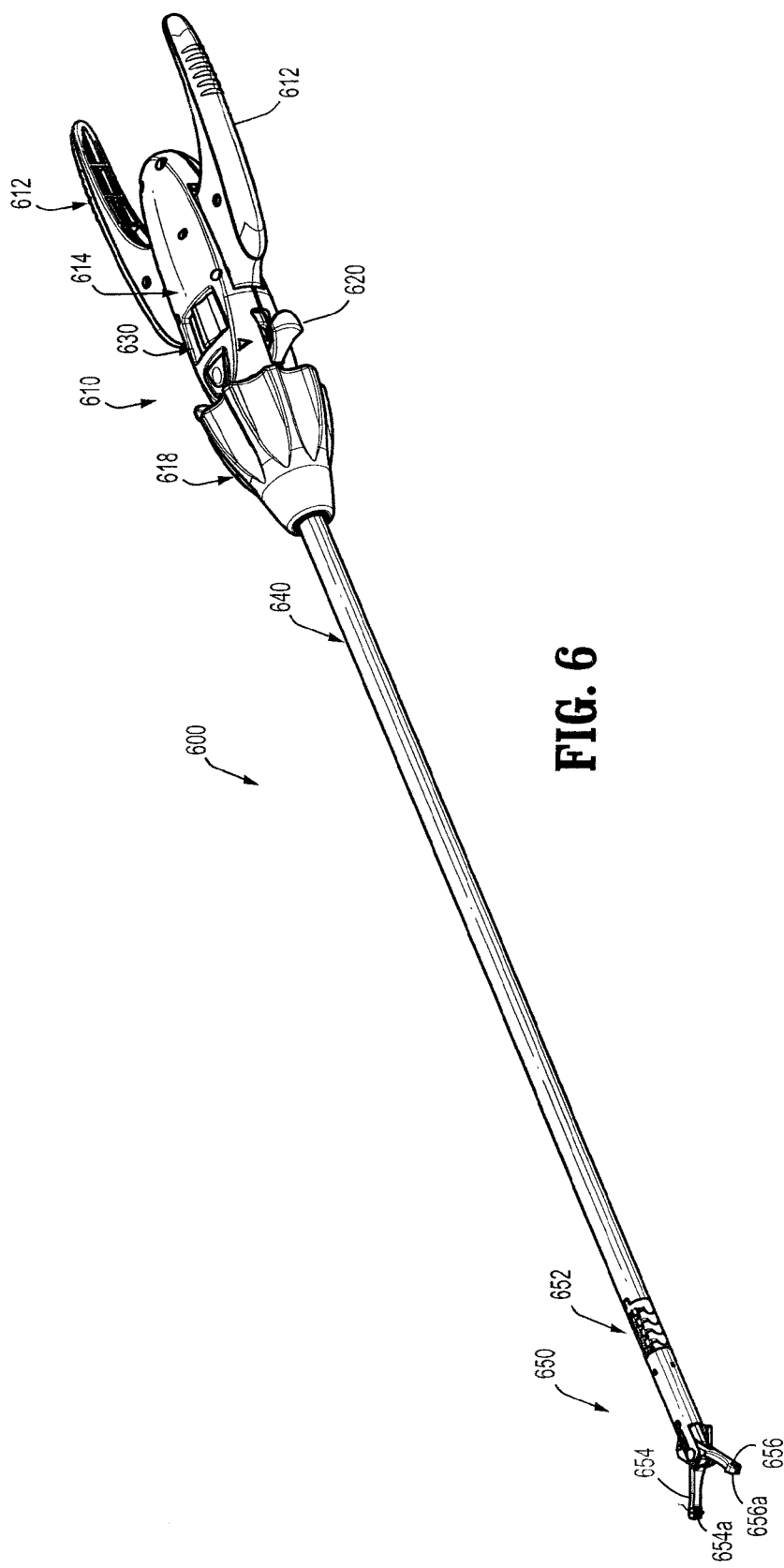
FIG. 6 is a perspective view of a stitching device.

An example of a suitable surgical apparatus is disclosed in U.S. patent application Ser. No. 12/482,049, which was filed on Jun. 10, 2009, the entire contents of which are hereby incorporated by reference. In particular, U.S. patent application Ser. No. 12/482,049 discloses a stitching device 600, as shown in FIG. 6. The stitching device 600 includes an end effector 650 that is supportable on or extends from a handle assembly 610 and/or a distal end of an elongate tubular body portion 640 extending distally from the handle assembly 610. The end effector includes a neck portion 652 supported on the distal end of shaft 640 extending from hand assembly 610. The end effector 650 further includes jaws 654, 656, which include respective needle receiving openings 654(*a*), 656(*a*). The handle assembly 610 further includes a tip rotation assembly 618 and an articulation assembly 630 rotatably supported in housing 614. The handle assembly 610 further includes a needle loading/retaining assembly 620 supported thereon. The handle assembly 610 further includes a pair of handles 612 pivotably secured to housing 614 and extending outwardly therefrom.

The suture loading package 100 includes a securement structure that may include one or more protrusions 104 that are configured and adapted to facilitate releasably securing the length of suture S prior to use. For example, the looped portion 1 of the length of suture S may be secured around each protrusion 104 or the length of suture S may be wrapped around one or more of the protrusions 104. The length of suture S is prepared for use by releasing the length of suture S from the protrusions 104 and loading the needle 12 into the suture needle loading mechanism 50. In addition, the protrusions help keep multiple lengths of barbed suture S separate and minimize tangling of the lengths of barbed suture S. The protrusions 104 may be spaced apart from one another. By spacing the protrusions 104 apart, the frictional interaction between the protrusions 104 and the length of suture S may be reduced. Moreover, the protrusions 104 may each have a different shape, e.g., arcuate or angled, that corresponds to a path defined by the arrangement of protrusions 104 for the length of suture S. Moreover, the coefficient of friction between the length of suture S and the protrusions 104 may be selected by selecting different materials. Depending on the coefficient of friction, the force necessary to slide the length of suture S past a protrusion 104 may be determined.

Figure 2:
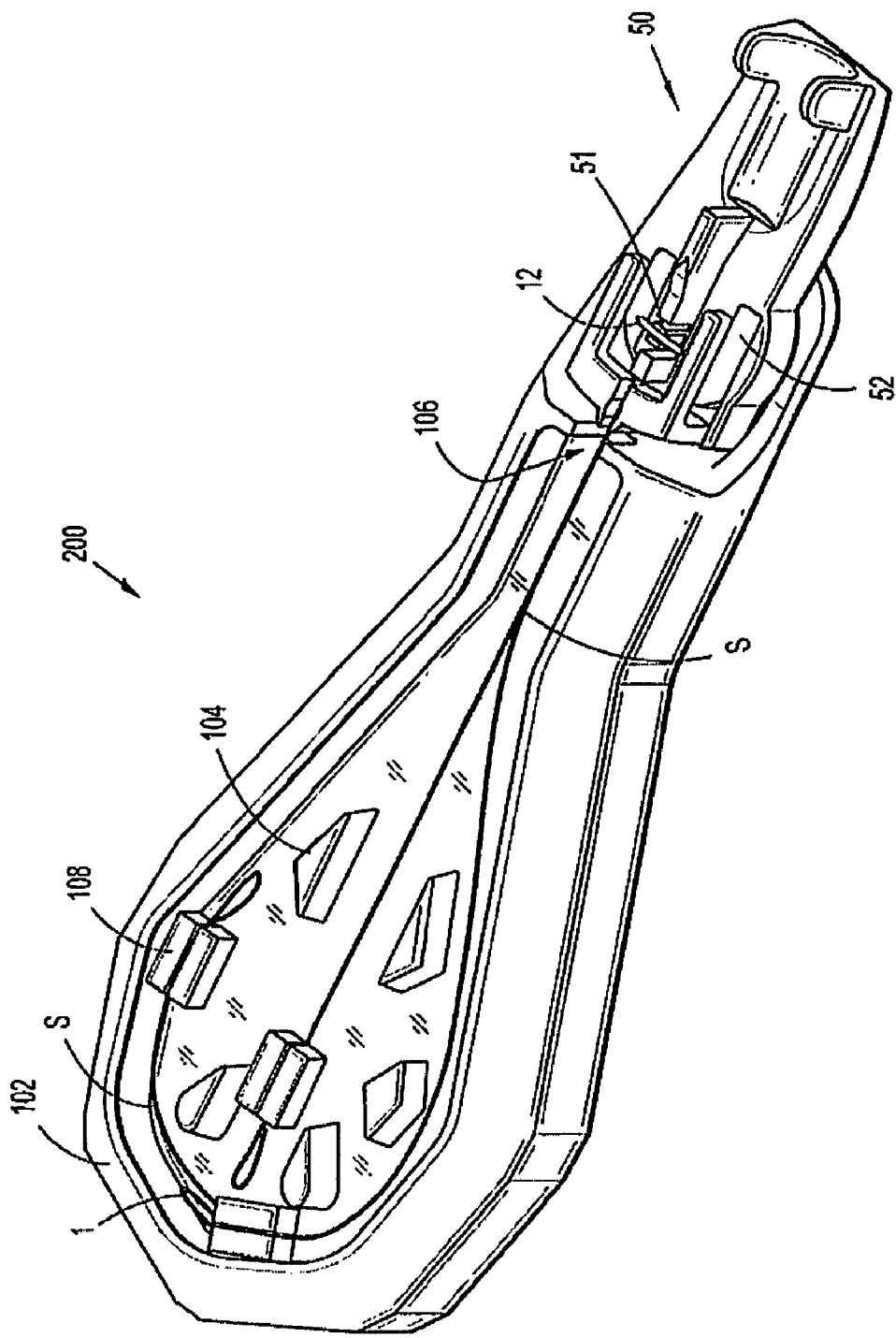
FIG. 2 is a perspective view of another embodiment of a suture loading package in accordance with the present disclosure shown with a suture needle loading mechanism.

Alternate structures for releasably securing the length of suture S within the body portion 102 include posts 108 (FIG. 2). For example, a suture loading package 200, shown in FIG. 2, is substantially identical to the suture loading package 100, however unlike the suture loading package 100, the suture loading package 200 includes one or more posts 108. The post 108 is configured and adapted to frictionally and releasably secure the length of suture S therein. As shown in FIG. 2, each post 108 defines a channel that is configured and adapted to receive the length of suture S therethrough. The dimensions of the channel may inhibit the translation of the looped portion 1 of the length of suture S through the channel defined by the post 108.

Figure 3:
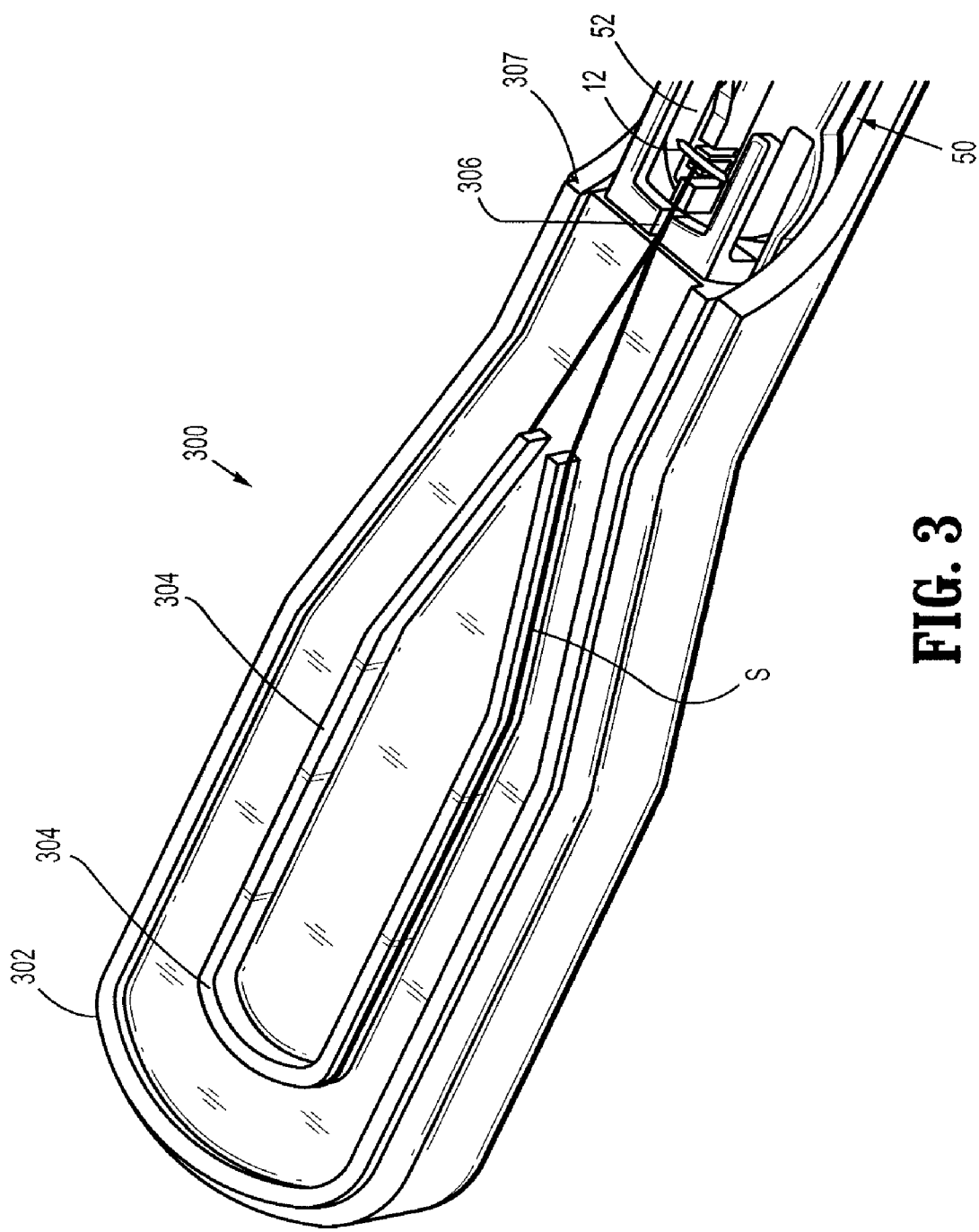
FIG. 3 is a perspective view of a further embodiment of a suture loading package in accordance with the present disclosure.

In another embodiment, a suture loading package 300 generally includes a body portion 302. The body portion 302 may be ergonomically shaped. As shown in FIG. 3, the body portion 302 has an elongated shape, which facilitates grasping of the suture loading package 300 by a user. A securement structure may include one or more guide contours 304 that are positioned within the body portion 302. The guide contours 304 are configured and adapted to releasably secure one or more lengths of suture S until ready for use. Upon pulling an end of the length of suture S, the configuration of the guide contours 304 is shaped to facilitate advancement of the length of suture S while minimizing tangling or a bottle-neck effect that may impede advancement of the length of suture S. An opening 306 at or near a proximal end 307 of the body portion 302 is adapted and configured to receive the length of suture S therethrough. A hub 52 is disposed at or near the proximal end 307 of the body portion 302 such that suture loading mechanism 50 may be positioned thereon.

As shown in FIG. 3, the guide contour 304 may be a continuous length of material that is extruded or protruded from a surface within the body portion 302. The degree of frictional engagement between the guide contours 304 and the length of suture S may be determined by the selecting materials having varying coefficients of friction. During use, a sufficient force is applied to the length of suture S to guide the length of suture S past the guide contour 304.

Figure 4:
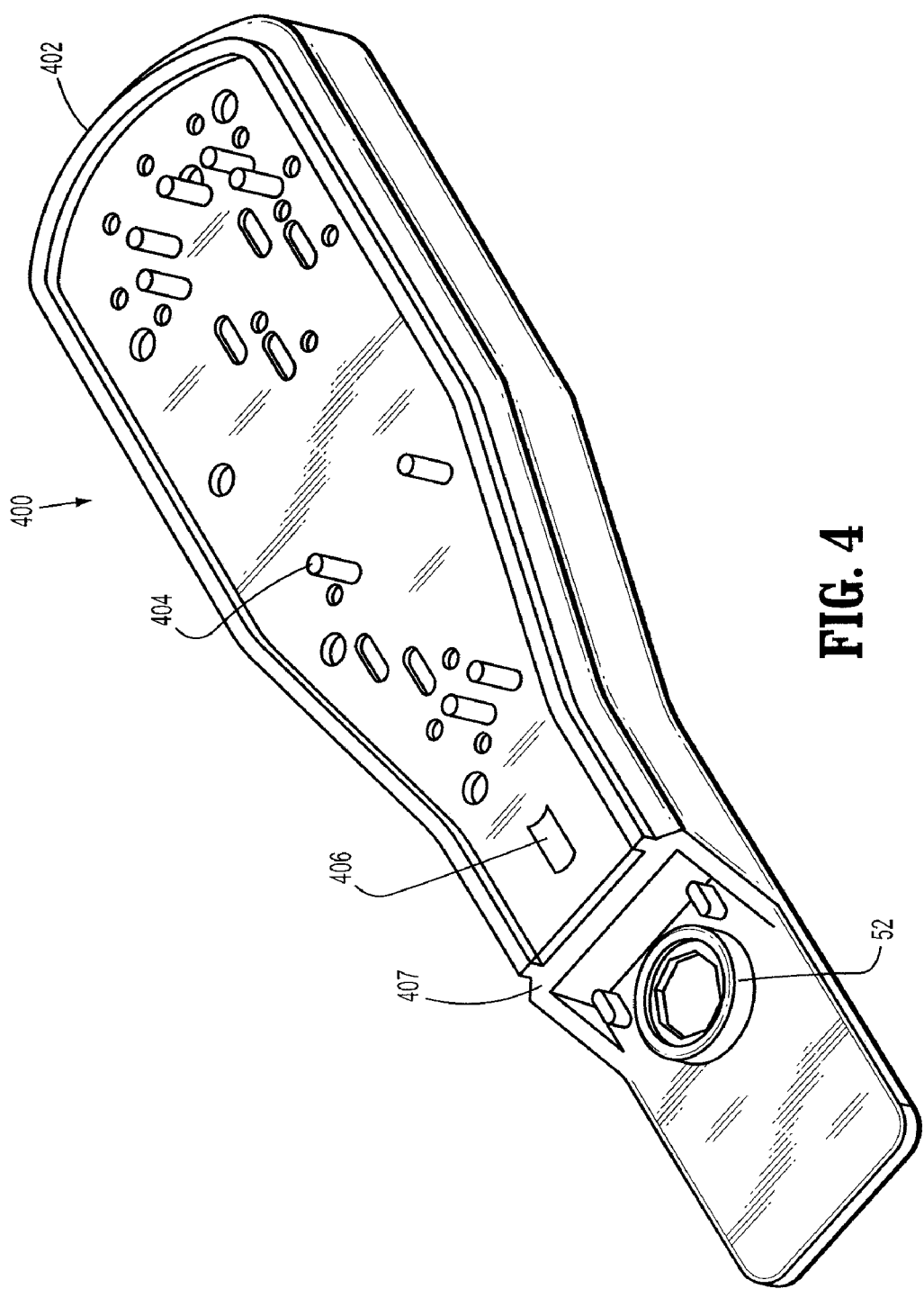
FIG. 4 is a perspective view of a still further embodiment of a suture loading package in accordance with the present disclosure.

A suture loading package 400 will now be described with reference to FIG. 4. The suture loading package 400 is substantially similar to the suture loading package 300 that was described above with reference to FIG. 3. Instead of utilizing guide contours 304 to store a length of suture S prior to use and to guide the length of suture S during deployment of the suture S, the suture loading package utilizes a securement structure including one more protrusions or prongs 404. The prongs 404 may be cylindrical protrusions as shown in FIG. 4. The looped portion 1 of the length of suture may be placed about a prong 404 or the length of suture may be wrapped around one or more of the prongs 404. A plurality of prongs 404 may define an equivalent path as that defined by the guide contours 304 of suture loading package 300 described above with reference to FIG. 3. The use of prongs 404 instead of guide contours may provide the user with the option of placing the looped portion 1 of the length of suture S about a prong 404 or alternatively or in addition to wrapping a length of suture S around one or more of the prongs 404. A channel 406 is disposed at or near proximal end 407 of the body portion 402. As shown in FIG. 4, the channel 406 may be an arcuate recess to facilitate guidance of the length of suture S to the proximal end 407 of the body portion 402. As described above with respect to the suture loading packages 100, 200, and 300, the suture loading package 400 includes a hub 52 that is disposed at or near the proximal end 407 of the body portion 402. The hub 52 is adapted and configured to receive, thereon, the suture loading mechanism 50.

Figure 5:
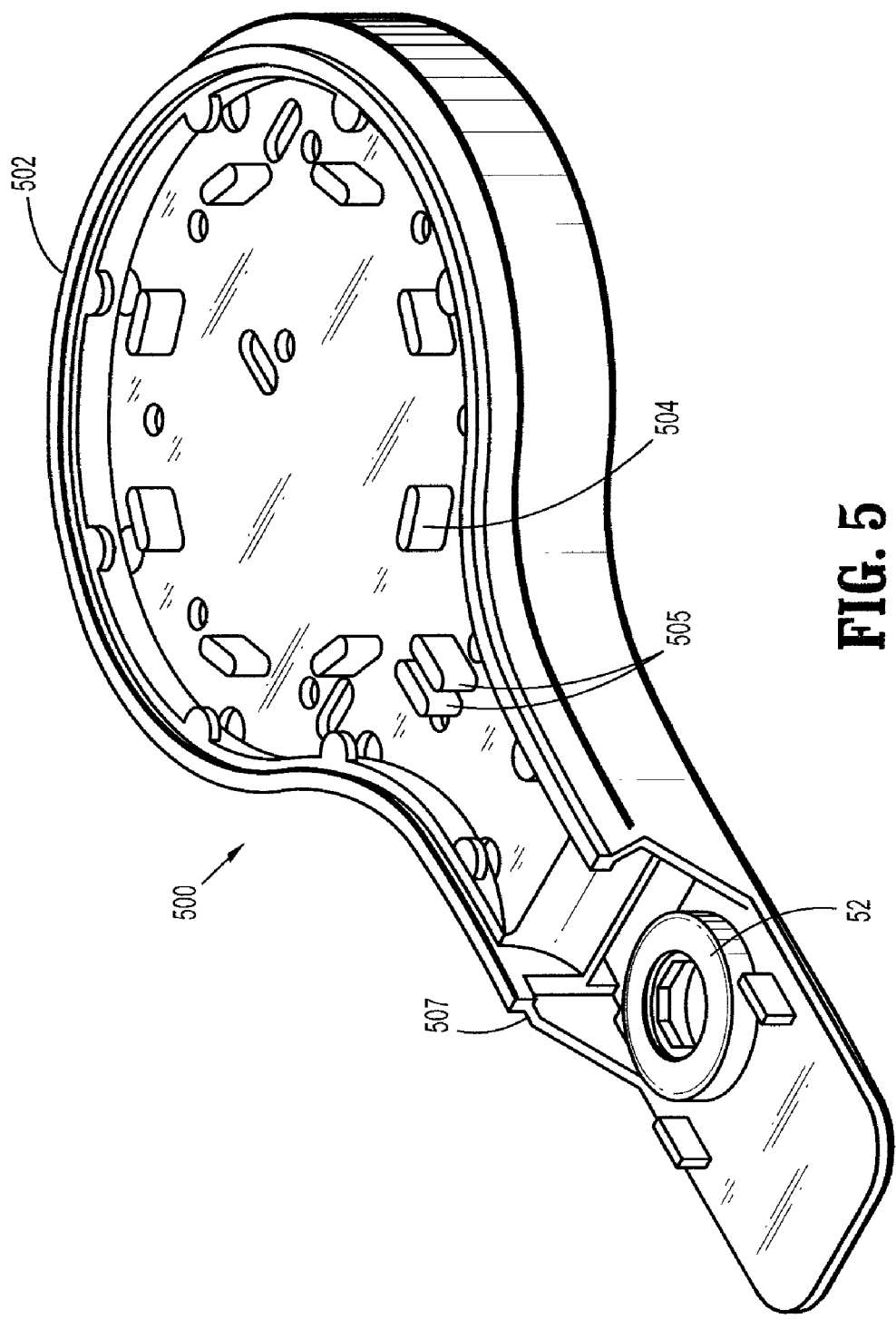
FIG. 5 is a perspective view of another embodiment of a suture loading package in accordance with the present disclosure.

In yet another embodiment, a suture loading package 500 will now be described with reference to FIG. 5. The suture loading package 500 generally includes a body portion 502 and a securement structure including one or more protrusions 504, 505 disposed therein. The body portion 502 may have a rounded or bulbous shape as shown in FIG. 5 to facilitate grasping of the body portion 502. The protrusions 504, 505 may have a generally rectangular or elliptical shape with rounded edges, as shown in FIG. 5, but are not limited to such a shape. The shape of the body portion 502 may generally approximate the shape of the path defined by a set of protrusions, i.e., protrusions 504, to minimize the size the body portion 502. As shown in FIG. 5, a first set of protrusions 504 is grouped to define an arcuate or circular contour and a second set of protrusions 505 is grouped to lead the one or more lengths of suture S toward a proximal end 507 of the suture loading package 500. The second set of protrusions 505 may be positioned substantially in parallel to one another to define a channel therebetween for the reception of the length of suture S. As described above with respect to suture loading packages 100, 200, 300, and 400, the protrusions 504, 505 may be utilized to place the looped portion 1 of the lengths of suture S thereabout until ready for use or may be used to provide a path around which to wrap the lengths of suture S. Moreover, as described above with respect to the suture loading packages 100, 200, 300, and 400, the suture loading includes a hub 52 that is configured and adapted to receive a suture loading mechanism 50 thereon.

Each suture loading package 100-500 is configured and adapted to store one or more lengths of suture S. When a length of suture S is ready to be used, the user can manually release the length of suture S from the attachment structure whether the attachment structure be a protrusion, e.g., protrusion 104, 304, 502 or prong 404, about which the looped portion 1 of the length of suture S is placed or about which the length of suture S is wrapped, or whether the attachment structure is a post 108, as shown in FIG. 2. Upon releasing the length of suture S from the attachment structure, the needle 12 of the length of suture S may be loaded into the suture loading mechanism 50 to facilitate subsequent loading of the suture S into a suitable surgical apparatus, such as the stitching device 600 (FIG. 6).

The suture loading mechanism 50 is configured and adapted to frictionally retain the needle 12 within a needle retaining member 51, as shown in FIG. 2. As described above, the needle 12 may be loaded onto a surgical apparatus, such as the stitching device 600. The needle retaining member 51 facilitates loading of the needle 12 onto the surgical suturing apparatus 10. With the needle 12 retained within the needle retaining member 51, loading of the needle 12 is achieved by aligning and placing the needle 12 into a selected needle receiving opening 654(*a*), 656(*a*) of respective jaws 654, 656. This process is repeated each time a suture-needle combination is loaded onto the surgical suturing apparatus 10.

It will be understood by those skilled in the art that various modifications and changes in form and detail may be made to the present disclosure without departing from the scope and spirit of the same. Therefore, the above description should not be construed as limiting, but merely as exemplifications of particular embodiments. While several embodiments of the disclosure have been shown in the drawings, it is not intended that the disclosure be limited thereto. Rather, the disclosure is intended to be read as broadly in scope as the art will allow.

What is claimed is:

1. A suture loading package, comprising:
    a body portion including a proximal end;
    a securement structure disposed within the body portion, the securement structure configured and adapted to releasably secure a length of suture;
    an opening at the proximal end of the body portion, the opening configured and adapted to receive the length of suture therethrough; and
    a hub disposed at or near the proximal end of the body portion, wherein the hub includes an annulus shaped protrusion having an inner wall defining a recess having an octagon shaped cross-section configured to engage with a suture loading mechanism.

2. The suture loading package of claim 1, wherein the securement structure is one or more protrusions.

3. The suture loading package of claim 2, wherein the one or more protrusions is adapted and configured to receive thereabout a looped portion of the length of suture.

4. The suture loading package of claim 2, wherein a plurality of protrusions define a path about which the length of suture may be wrapped.

5. The suture loading package of claim 1, further comprising a post that is configured and adapted to frictionally and releasably secure the length of suture therein.

6. The suture loading package of claim 1, wherein the length of suture is operably coupled to a needle.

7. The suture loading package of claim 2, wherein the body portion is ergonomically shaped.

8. The suture loading package of claim 1, wherein the body portion is elongated.

9. The suture loading package of claim 1, wherein the length of suture includes a looped portion.

10. The suture loading package of claim 9 further comprising a prong, the looped portion receivable by the prong.

11. The suture loading package of claim 1, wherein the securement structure is a guide contour that is shaped to facilitate advancement of the length of suture along the guide contour.

12. The suture loading package of claim 1 further comprising a set of protrusions that are placed in an arrangement to lead the length of suture to the proximal end of the body portion.

13. The suture loading package of claim 6, wherein the suture loading mechanism is configured to facilitate loading of the needle onto a surgical apparatus.

* * * * *